United States Patent [19]

Policastro et al.

[11] Patent Number: 5,012,411
[45] Date of Patent: Apr. 30, 1991

[54] APPARATUS FOR MONITORING, STORING AND TRANSMITTING DETECTED PHYSIOLOGICAL INFORMATION

[75] Inventors: Charles J. Policastro, 2122 Old Forde Way, Lansdale, Pa. 19446; Edmond J. Dougherty, Philadelphia, Pa.; Martin J. Dowling, Haddonfield, N.J.

[73] Assignee: Charles J. Policastro, Lansdale, Pa.

[21] Appl. No.: 757,965

[22] Filed: Jul. 23, 1985

[51] Int. Cl.$^5$ ............................................. A61B 5/04
[52] U.S. Cl. .................................. 364/413.06; 128/710
[58] Field of Search ................. 364/415, 417; 128/709, 128/710, 711

[56] References Cited

U.S. PATENT DOCUMENTS

| | | | |
|---|---|---|---|
| 3,782,367 | 1/1974 | Hochberg et al. | 128/697 |
| 3,972,320 | 8/1976 | Kalman | 364/415 |
| 3,991,747 | 11/1976 | Stanly et al. | 128/697 |
| 4,090,505 | 5/1978 | Mortana | 364/417 |
| 4,123,785 | 10/1978 | Cherry et al. | 360/4 |
| 4,173,971 | 11/1979 | Karz | 128/702 |
| 4,193,393 | 3/1980 | Schlager | 128/710 |
| 4,214,590 | 7/1980 | Patnoi et al. | 128/710 |
| 4,216,462 | 8/1980 | McGrath et al. | 364/415 |
| 4,231,374 | 11/1980 | Hudek et al. | 128/702 |
| 4,270,547 | 6/1981 | Steffin et al. | 364/415 |
| 4,333,475 | 6/1982 | Moreno et al. | 128/711 |
| 4,378,021 | 3/1983 | Strand | 128/709 |
| 4,417,306 | 11/1983 | Citron et al. | 364/415 |
| 4,449,536 | 5/1984 | Weaver | 364/417 |
| 4,483,346 | 11/1984 | Slavin | 128/710 |
| 4,494,557 | 1/1985 | Little et al. | 364/415 |
| 4,519,398 | 5/1985 | Lisiecki et al. | 128/710 |
| 4,527,567 | 7/1985 | Fischler et al. | 128/697 |
| 4,577,639 | 3/1986 | Simons et al. | 128/709 |
| 4,622,979 | 11/1986 | Kochis et al. | 128/702 |

OTHER PUBLICATIONS

"A Computer System for Capturing Transient Electrocardiographic Data," Kenneth L. Ripley and Jerome R. Cox, Jr., *Computers in Cardiology Conference—IEEE*, 1976.

*Primary Examiner*—Jerry Smith
*Assistant Examiner*—Kim Thanh Tbui
*Attorney, Agent, or Firm*—Panitch Schwarze Jacobs & Nadel

[57] ABSTRACT

A portable, self-contained, microprocessor controlled apparatus for monitoring, storing and transmitting detected physiological information, including an input section for sequentially receiving analog signals corresponding to heart activity for as many as twelve different cardiac sensors. An input section is provided for receiving analog electrical signals corresponding to blood pressure from at least one sensor. An analog to digital converter is provided for converting the received analog signals to a series of digital pulses at a predetermined sampling rate and for receiving and storing the digital pulses in predetermined memory locations. A control section is provided for recalling the stored digital pulses from the memory and for receiving the recalled digital pulses and for transmitting them to a remote location over a communications system. In the preferred embodiment, the input section is for receiving analog signals corresponding to cardiac conductivity, brainwave activity, blood pressure, blood flow and other ultrasonic cardiovascular and intracranial data. The latter signals are also converted to digital form for storage and later recall and transmission to a remote location.

19 Claims, 1 Drawing Sheet

APPARATUS FOR MONITORING, STORING AND TRANSMITTING DETECTED PHYSIOLOGICAL INFORMATION

BACKGROUND OF THE INVENTION

The present invention relates to an apparatus for monitoring, storing and transmitting detected physiological information and, more particularly, to such an apparatus which is portable, self-contained and microprocessor controlled.

There is an urgent need for a small, light weight, self-contained device for monitoring, storing and transmitting detected physiological information, particularly information considered critical in analyzing the condition of a patient. Such information includes electrocardiogram information, echogram information, electroencephalogram information, blood pressure information, and other related physiological information. By having such information instantly available, a physician can evaluate the immediate condition of a patient in order to make an informed diagnosis with regard to the patient's physiological condition and any reported symptoms. By combining this information with the patient's previous history, a physician may be able to treat the patient's condition without having to repeatedly send the patient to the hospital.

While the devices presently available permit a physician or medical technician to monitor one or more different types of such physiological information, they are inadequate for several reasons. The available devices are generally large in size, heavy in weight, and require a highly trained health professional to be physically present with the patient when the data is being acquired. Due to the transient nature of many symptoms, which can occur at any time of the day or night, it is difficult, impractical, and expensive to have a health care professional transport the other devices to the patient or to have the patient go to a hospital whenever a symptom is reported. In addition, many of the presently available devices are relatively inefficient with respect to energy usage and, therefore, must generally be plugged into an AC wall outlet, thereby further hampering the portability of the device. Moreover, many of the prior art monitoring devices which are portable do not have the capability of storing a significant amount of physiological information. Thus, the physician or other health care professional must be located with the patient to obtain the information from the device or the information must somehow be relayed to the physician or other health care professional. This is particularly applicable to the many existing devices which are adapted for the direct transmission of the data over an existing communications system, such as a telephone.

Furthermore, many existing ECG monitoring devices are limited in their capability. For example, although there are various types of cardiac monitoring devices presently available, for the most part, these devices are only capable of receiving information from a single ECG lead or, at most, a limited number of ECG leads, such as four ECG leads. Thus, the current devices only provide the physician with a small portion of the required information needed to make a diagnosis and to establish adequate therapy.

The present invention provides a small, light weight battery powered apparatus for monitoring, storing and transmitting detected physiological information concerning a patient. The apparatus is battery powered and self-contained and provides the ability both to store the physiological information in its own internal memory and to transmit the physiological information over an existing communication system, such as a telephone line. Alternatively, the present invention can display the physiological information on its built-in graphic display or can provide a permanent record of the information with its optional built-in graphic printer. It also provides the individual operator, be it a health care professional or the patient, the ability to actually visualize on the real time graphic display the actual information being recorded. This allows the operator to verify the quality of the information as it is being stored and, if necessary, adjustments to the lead placement can be made prior to the transmitting of data. This reduces the need for repetitive data samples due to artifact, AC interference, somatic tremor, and base line wandering, which are generally encountered with the present devices.

The present invention is capable of receiving, storing and transmitting a full twelve lead ECG signal and/or an eight lead EEG signal, as well as information pertaining to the patient's blood pressure, blood flow, and other ultrasonic data pertaining to the cardiovascular system and/or intracranial processes. In addition, selected information may be transmitted "live" and in "real time," if desired.

Due to its internal memory, the present invention permits the storage of pre-event information. For example, if a patient is having a symptomatic event, such as chest pain, dizziness, numbness, or headaches, stored cardiac or cerebral information indicating the physiological condition of the patient for a predetermined time prior to the occurrence of the symptomatic event can be retained for later analysis by a physician, or other health care professional.

The present invention is particularly useful when employed in a retirement home or nursing home. Generally, nursing homes do not have a physician permanently located on the premises, therefore, when a patient is in distress the physician is called for advice. Since the physician generally does not have all of the information required to make a diagnosis—the patient is referred to a hospital. If the distress is transient, the physician may request that an ECG, EEG or other form of physiological testing be performed. It can take as long as seven days before the physician receives the results from this type of testing. By this time, the patient may have experienced many uncomfortable hours of physical discomfort or pain due to the nature of the symptoms. The present invention permits the physiological information to be taken and recorded at will. Thereafter, the present invention may be taken to the nearest telephone and the information transmitted over the telephone line to a remote location for immediate evaluation by a physician or other health professional.

Because the present invention is light weight, self-contained and portable, it can be worn by an ambulatory patient without discomfort or inconvenience. The device can also be conveniently carried by physicians as they go on their rounds or on visitations. The present invention enables the physician to immediately obtain up-to-the-minute physiological information concerning the patient.

The present invention also has the capability of obtaining and storing patient baseline data, as well as other important patient information, such as name, age, sex, physician's name, present medications and the like. The present invention may be programmed to continuously compare incoming physiological information with the previously stored baseline data and to generate a warning signal in the event that the comparison indicates that the present physiological information deviates from the baseline information by more than a predetermined amount. The doctor or other health professional can determine the permissible deviation limits.

SUMMARY OF THE INVENTION

Briefly stated, the present invention comprises a portable, self-contained microprocessor controlled apparatus for monitoring, storing and transmitting detected physiological information. The apparatus comprises means for sequentially receiving analog signals corresponding to heart activity from as many as twelve different cardiac sensors and means for receiving analog electrical signals corresponding to other physiological data. Means are provided for converting the received analog signals to a series of digital pulses at a predetermined sampling rate. Memory means are provided for receiving and storing the digital pulses in predetermined memory locations. Means are provided for recalling the stored digital pulses from the memory means and for transmitting the digital pulses to a remote location over a communication system. In the preferred embodiment, the present invention further includes means for detecting the presence of a pacer signal and for generating digital pulses upon the occurrence of pacer signals and an optional printer means for providing a printed output representative of any physiological information being received and stored. The preferred embodiment also includes means for sequentially receiving analog signals corresponding to brain activity from a plurality of sensors for storage in the memory means and means for receiving the digital pulses from the memory means for converting the pulses to analog form and for displaying the analog signals to provide a graphic representation of the physiological information.

DESCRIPTION OF THE DRAWING

The foregoing summary, as well as the following detailed description, will be better understood when read in conjunction with the appended drawing. For the purpose of illustrating the invention, there is shown in the drawing an embodiment which is presently preferred, it being understood, however, that this invention is not limited to the precise arrangement shown.

In the drawing.

DESCRIPTION OF A PREFERRED EMBODIMENT

Figure 1:
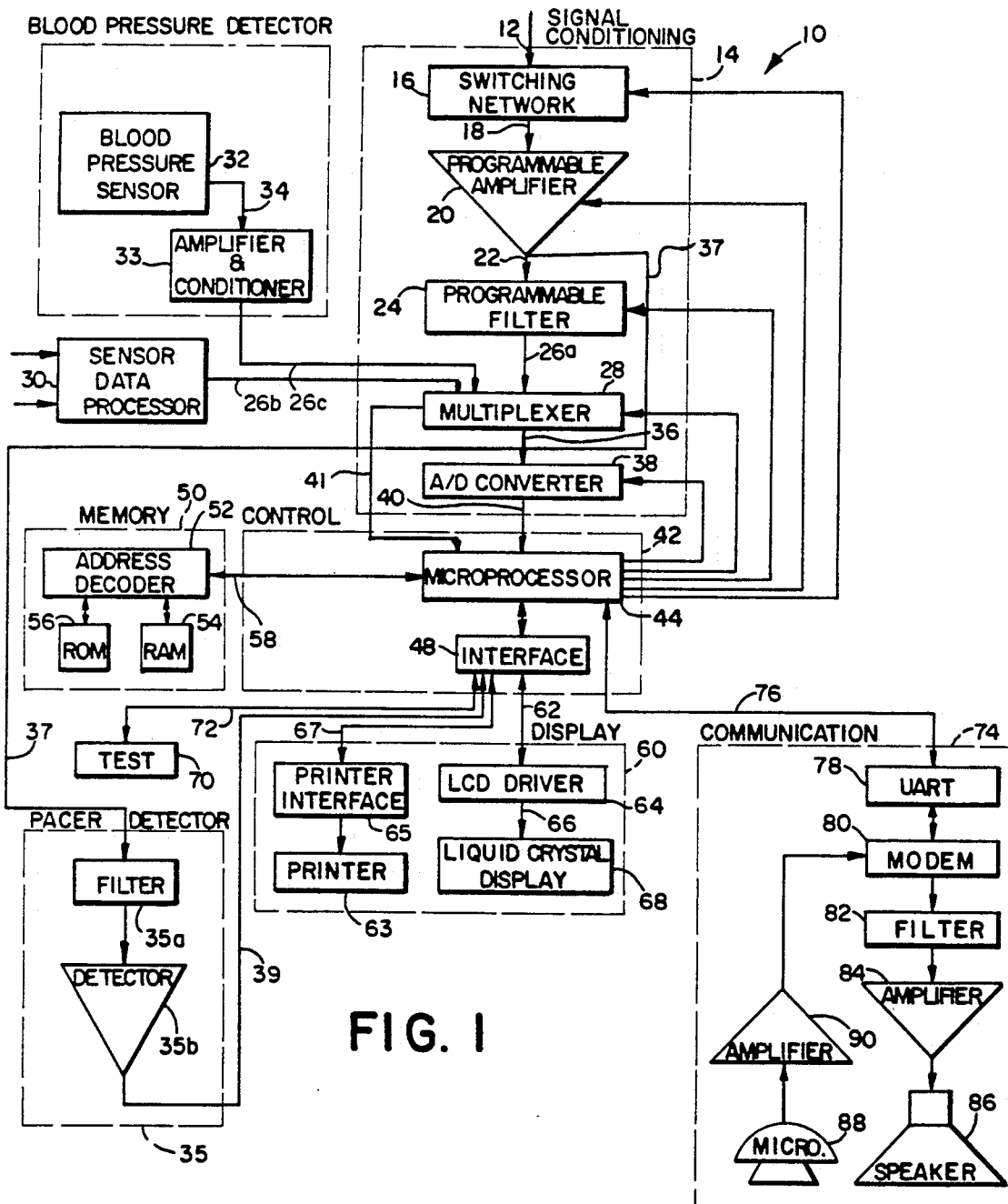
FIG. 1 is a schematic block diagram of a portable, self-contained, microprocessor apparatus for monitoring, storing and transmitting detected physiological information in accordance with the present invention.

Referring now to FIG. 1, there is shown a schematic block diagram representation of an apparatus for monitoring, storing and transmitting physiological information, generally indicated as 10, in accordance with the present invention. The apparatus 10 is a small, portable, self-contained, microprocessor controlled device which may be employed for monitoring a variety of physiological information, including, for example, ECG, EEG, blood pressure, heart rate information, and other information or data pertaining to the cardiovascular system and/or intracranial processes, preferably ultrasonically obtained, and for storing the information and data in an internal memory system.

The present embodiment of the invention may be employed in connection with a single standard ECG or EEG lead (with a reference lead to establish a common or ground) 12, or with as many as twelve such leads (not shown). The single lead 12 or the plurality of leads (not shown) are each connected on one end to a senor or electrode (not shown) which is secured to the patient being monitored in the usual manner. The other end of each of the leads 12 is connected to the apparatus 10 utilizing a standard connector (not shown) of the type which is normally used in making such lead connections. For the purpose of illustrating the structure and operation of the present invention, the following description relates to a single lead 12, it being understood that the apparatus 10 may be employed with as many as twelve such leads.

The electrode (not shown) senses heart or brain wave activity in a manner well known in the art, and generates low voltage analog electrical signals which are proportional to the activity sensed. The analog electrical signals from the electrode are conducted along the lead 12 to the apparatus 10. Within the apparatus 10, the analog electrical signals first enter signal conditioning circuitry, shown collectively as 14, for initial processing and for converting to digital form. The signal conditioning circuitry 14 includes a front end switching network 16 which is employed for switching or multiplexing the signals received from multiple ECG or EEG leads (not shown) when multiple leads are employed. When the multiple leads are employed, the switching network 16 operates to sequentially receive and pass the signals from each lead on a time division basis, the signals from each lead being received and sequentially passed for a predetermined time, for example, fifteen seconds. The output of the switching network 16 is connected by a plurality of lines shown collectively as line 18 to a programmable amplifier 20.

The programmable amplifier 20 is microprocessor controlled and operates to amplify and adjust the amplitude of the analog signals received from lead 12 to a predetermined level for further processing. The predetermined amplitude level is obtained by setting the gain of the programmable amplifier 20 to an initial level and then increasing the gain by a series of predetermined steps until the amplifier 20 becomes saturated. In the present embodiment, each of the predetermined steps increases the gain of the amplifier 20 to generally twice the gain afforded by the previous step. The gain of the programmable amplifier 20 is increased by changing the resistance of a gain resistor (not shown) from a relatively high resistance, for example, 9.76K ohms to progressively lower resistance, for example, 4.87K 2.43K, 1.21K ohms, etc., each of which is about one-half of the resistance of the previous resistor. The resistance value of the gain resistor is changed by a switching network or multiplexer (not shown) which is controlled by a programmed microprocessor through a programmable interface adapter (not shown) to switch gain resistors into and out of the amplifier circuit. The microprocessor also monitors the output gain of the programmable amplifier 20 to determine when the amplifier becomes saturated.

Once the programmable amplifier 20 reaches saturation, the amplifier gain is decreased by one step (i.e., reduced by one-half) to bring the amplifier out of saturation and to establish the gain setting required to provide the predetermined amplitude for the analog signals from the particular lead 12. Thereafter, the particular gain setting is stored in a predetermined memory location for later recall. Of course, when multiple leads are employed, the amplitude of the received analog signals for each lead must be separately adjusted to establish a setting for the programmable amplifier 20 for each lead. Each of the programmable amplifier gain settings is stored in its own predetermined memory location for recall at the appropriate time to reset the gain of the programmable amplifier 20 each time the signals for the particular corresponding lead are received from the switching network 16 for processing.

The output of the programmable amplifier 20 is attached by a suitable conductor or line 22 to a programmable filter 24. The programmable filter 24 is provided to filter out or remove unnecessary and/or undesirable signals and transients, such as muscle noise, etc. In the present embodiment, the programmable filter 24 is of the band pass type and may be programmed to pass a band between 0.05 Hz and 100 Hz or a band between 0.05 Hz and 50 Hz. The bandwidth of the programmable filter 24 is changed by varying the resistance value of an associated resistance network (not shown). The resistance value of the resistance network is varied by a switching network or multiplexer (not shown) which is controlled by a programmed microprocessor through a programmable interface adapter (not shown) to switch resistors (not shown) into or out of the resistance network. The microprocessor is responsive to the selection of the desired bandwidth by the operator, doctor, or other health care professional. The output signal from the programmable filter 24 comprises an analog signal of a predetermined amplitude and of a narrow, predetermined bandwidth.

The output signal from the programmable filter 24 is passed or transmitted along line 26a to one input of a multiplexer 28. The multiplexer 28 may also receive other input signals from other sources along lines 26b, and 26c. The other sources may be sensors which provide similar analog electrical signals proportional or corresponding to other desired physiological characteristics. The multiplexer 28 which, in the present embodiment is of the time division type, is controlled by the microprocessor and is employed for multiplexing the various analog signals for transmission to the remainder of the apparatus 10, as discussed below.

In the present embodiment, line 26b is connected to a sensor data processor 30. The sensor data processor is connected to one or more sensor leads (not shown) for receiving signals pertaining to other cardiovascular system data or intracranial processes. Preferably, the sensors (not shown) are of the ultrasonic type, which may include a processing device. Of course, any other suitable type of sensor with or without a processing device may alternatively be employed.

Line 26c is connected through appropriate amplifier and conditioning circuitry 33 to a blood pressure sensor 32. Basically, the blood pressure sensor 32 is used in measuring blood pressure. The blood pressure sensor 32 includes a blood pressure cuff (not shown) which is periodically inflated and deflated and a sensor for detecting the blood flow and pressure through the veins to determine the blood pressure of the individual being monitored. The microprocessor is programmed to recognize systolic and diastolic conditions. At these points, the microprocessor reads the blood pressure sensor (via multiplexer and A/D converter) and stores the values in memory for later transmission and/or display.

Line 37 is employed for conducting the output of the programmable amplifier 20 directly to the pacer detection circuit 35, bypassing the programmable filter 24. The pacer detection circuit 35 includes a filter 35a and a threshold detector 35b. The filter 35a is employed to pass only those signals generated by a pacer (not shown). In the preferred embodiment, the filter is a high pass filter of the type which passes signals having a frequency greater or equal to the pacer signal (for example, 1 KHz). The pass frequency is adjustable so that all common pacer signals can be detected. The threshold detector 35b is employed to condition the pacer signal for transmission to the microprocessor. The microprocessor is programmed to insert the pacer signal at the appropriate memory location so that the pacer signal will be seen at the appropriate location in the ECG waveform, when the ECG is displayed or transmitted for display and review by the doctor or other medical professional.

Output signals from the multiplexer 28 are passed along a conductor or line 36 to an analog to digital (A/D) converter 38. In the present embodiment, the A/D converter 38 is of the eight bit serial type and is employed to convert the incoming analog signals into a series of digital pulses. The A/D converter operates at a predetermined sampling rate to provide digital pulses having a predetermined width and with a predetermined spacing between the pulses. In order to prevent the loss of any significant physiological information contained in the received analog signals, the A/D converter 38 utilizes a sampling rate which is relatively high. In the presently preferred embodiment the sampling rate is on the order of 300 Hz.

In the present embodiment, the A/D converter 38 is a typical eight bit A/D converter of the type which is generally well known in the art and which may be purchased commercially from a variety of manufacturers. In the presently preferred embodiment the A/D converter 38 is an integrated circuit model TLC549IP which is produced and sold by Texas Instruments. A detailed discussion of the structure and operation of the A/D converter is not necessary for a complete understanding of the present invention and is available from the manufacturer. Basically, the A/D converter 38 receives the filtered analog signals at the predetermined amplitude level and converts them to a series of spaced digital pulses corresponding to the amplitude of the input analog signals.

The digital pulses from the A/D converter 38 are transmitted along line 40 to the control circuitry portion 42 of the apparatus 10. The heart of the control circuitry portion 42 is a microprocessor 44. In the presently preferred embodiment, the microprocessor 44 is of a type well known in the art and preferably is a model GS65C02 which is produced and sold by GTE Corporation. Complete details of the structure and operation of the microprocessor 44 are available from the manufacturer and will not be included in the present application since they are not necessary for a complete understanding of the present invention.

Associated with the microprocessor 44 is a digital interface 48. Like the microprocessor 44, the digital interface is of a type generally well known in the art and commercially available. Details of the structure and operation of the digital interface 48 are available from the various manufacturers. The microprocessor 44 receives signals from the pacer detection circuit 35 through the digital interface 48 along line 39.

The apparatus 10 further includes a memory circuit portion 50. As shown in FIG. 1, the memory circuitry includes an address decoder 52, random access memory (RAM) 54, and read only memory (ROM) 56. The microprocessor 44 is connected to the address decoder 52 through a plurality of conductors shown collectively on FIG. 1 as line 58. The address decoder 52 operates in the normal manner to permit the microprocessor 44 to access both the RAM 54 and the ROM 56 for reading and writing data and instructions. The address decoder 52 is of the type which is generally well known and commercially available from a variety of manufacturers. A detailed discussion of the structure and operation of the address decoder 52 is not necessary for a complete understanding of the present invention, and therefore will not be presented.

Likewise, the RAM 54 and the ROM 56 of the present embodiment are also generally well known commercially available products. A complete description of the structure and operation of the RAM 54 and the ROM 56 is not necessary for an understanding of the present invention and, therefore, will not be presented. The ROM 56 is employed for the storage of data and instructions, including a program for the operation of the apparatus 10 as controlled by the microprocessor 44. Similarly the RAM 54 is employed for the storage of data and instructions utilized in the operation of the apparatus 10.

The digital interface 48 is employed to provide digital communication between the microprocessor 44 and display circuitry 60 along a plurality of conductors or lines shown collectively as line 62. The display circuitry includes a liquid crystal display (LCD) driver 64 which is connected through a plurality of lines shown collectively as line 66 to a dot matrix liquid crystal display (LCD) 68. The LCD driver 64 is of the type generally known in the art and commercially available. A complete description of the structure and operation of the LCD driver 64 is available from the manufacturer and, therefore, will not be presented. The LCD driver 64 receives digital signals from the microprocessor 44 through the digital interface 48 and conditions the digital signals for display of the information by the liquid crystal display 68.

In the present embodiment, the liquid crystal display 68 comprises a dot matrix type graphic display which is employed for displaying waveforms, such as ECG or EEG waveform traces and other graphic information as will hereinafter be described. In addition, alpha numeric characters such as heart rate and diagnostic messages about the status of the apparatus 10 can be displayed.

The display circuitry 60 also optionally includes a miniature graphic printer 63 and a printer interface 65 which is connected to the digital interface 48 by a plurality of lines shown collectively as line 67. The printer 63 is of a well known type which is commercially available. The printer 63 is employed to provide a more permanent, hard copy of the physiological information which is received and stored by the apparatus 10. The printer interface 65 is also of a type generally well known and commercially available and is employed for receiving signals from the microprocessor 44 and placing the signals into the proper format for the printer 63. In this manner the printer 63 may be employed for providing a standard ECG strip showing the various ECG and EEG waveforms, printed readout of blood pressure, etc.

The digital interface 48 is also connected to test circuitry 70 by way of a plurality of conductors or lines shown collectively as line 72. The test circuitry 70 is employed for testing various structural and operational aspects of the apparatus 10. Aspects of the apparatus 10 which may be tested include electrodes 12, the programmable filter 24, A/D converter 38, ROM 56, RAM 54 and the battery (not shown) which is employed to provide power to the apparatus 10. Information concerning the status of the various aspects of the apparatus 10 which have been tested may be displayed on the liquid crystal display 68. For example, if it is determined that the battery is getting unacceptably weak, a suitable message such as "low battery power" may be displayed on the liquid crystal display. Preferably, the low battery warning will flash on and off intermittently to attract the attention of the user. The test circuitry 70 also operates to test the communication link between the apparatus 10 and the communication equipment at the remote location. In the event that there is a disruption in the communication link, the liquid crystal display is intermittently flashed on and off to attract the attention of the patient to correct the communication problem and/or to retransmit the data.

The apparatus 10 is also adapted to automatically shut itself off after the low battery warning has been flashed for an extended period of time, in the present embodiment, about two hours. The automatic shut-off feature is also employed to power down the apparatus 10 when checks by the microprocessor 44 indicate that no analog signals are being received by the apparatus 10. For example, when monitoring heart activity, the microprocessor 44 checks for periodic electrical signals above a certain threshold which occur with some regularity. If no such signals are obtained for a predetermined period of time, the apparatus 10 is automatically powered down. Of course, when in the low power or "off" mode, the apparatus 10 still maintains the RAM 54 so that no previously stored information is lost. Moreover, if the RAM 54 is of the volatile type, the apparatus 10 includes a back-up battery (not shown) to preserve the signals stored in the memory even if the primary battery (not shown) is exhausted or otherwise fails.

The apparatus 10 also includes built-in circuitry 74 for two-way communication between the apparatus 10 and a remote location. With the present embodiment, such communication is preferably by way of an existing telephone line (not shown). However, other forms of communication, for example, radio wave communication, cellular telephone communication, etc. (not shown) may alternatively be employed. The communication circuitry 74 permits the patient or user of the device 10 or any other individual such as a nurse, paramedic, or the like, to transmit signals representative of physiological information to a remote location such as a centrally located nurses' station, hospital, doctor's office, cardiac monitoring center, or the like. In this manner, a trained professional at the remote location can monitor the patient's condition for the purpose of evaluating the information received, so that some form of treatment can be suggested by the medical professional. This information can either be transmitted directly to a physician by using the receiving capabilities of a device identical to the one being used by the patient or it can be transmitted to a central base station.

The communication circuitry 74 of the present embodiment includes a universal asynchronous receiver transmitter or UART 78 which is connected to the microprocessor 44 along a plurality of lines shown collectively as line 76. The UART 78 receives digital signals in parallel from the microprocessor 44 and converts them to serial form for transmission. The UART 78, in turn, is connected to a high speed modem 80, preferably of the phase shift keying type, which receives and modulates the serial digital signals for transmission along a telephone line or some other type of communication or data transmission means. Preferably, the signals are transmitted at a rate of 2400 baud to provide a display at the remote location which is equal to real time. The output of the modem 80 passes through a filter 82, and an amplifier 84. A speaker 86 and a microphone 88 are used in the preferred embodiment of acoustical coupling to a telephone line. (If acoustically coupling, current technology permits only 1200 band transmission rates—this is due primarily to the low quality of telephone handsets.) The speaker 86 is of the type designed to interconnect with a standard telephone handset (not shown). Alternately, the modem can be connected directly to the telephone line, thus avoiding the need for an acoustic coupling.

The UART 78, modem 80, filter 82, amplifier 84 and speaker 86 are all components of the type which are generally well known in the art and are commercially available from a variety of manufacturers. Complete details of the structure and operation of each of these components are generally well known and available from the manufacturers and elsewhere, and are not necessary for a complete understanding of the present invention. These components cooperate in a known manner to serially transmit digital data signals received from the microprocessor 44 along a standard telephone line (not shown) for reception, conversion and analysis at a remote location.

For situations in which acoustical coupling is preferred, the communication circuitry 74 also includes a microphone 88 which is similarly adapted to interface with a standard telephone handset (not shown). The output of the microphone 88 is connected to an amplifier 90 and thereafter to the modem 80 and UART 78. In this manner, the monitor is acoustically coupled to the telephone line. The microphone 88 and amplifier 90 are also components of a type which are generally well known in the art and commercially available from a variety of manufacturers. The microphone 88 is not required in the case of direct coupling.

The modem 80 and UART 78 permit signals transmitted from a remote location along a telephone line (not shown) to be conditioned, demodulated and fed in parallel to the microprocessor 44. In this manner, two-way communication between the transmitting device and a like device for receiving information at the remote location is possible via the interconnecting telephone lines or other transmission means (not shown).

The communication circuitry 74 is employed to transmit calibration data, as well as test signals, to check on the proper operation of the communication link. In the event that the communication line between the apparatus 10 and the remote location is improperly established or becomes improperly established, the liquid crystal display will flash a warning to the patient. In addition, if the physician at the remote location wishes to talk to the patient, for example, to request that the information be resent, a signal can be sent to the apparatus 10 to cause the liquid crystal display 68 to flash a warning to the patient, indicating that the patient should speak over the communication system to the doctor. The communication circuitry 74 is also employed to send the more general patient data to the remote location. Such patient data includes the name of the patient, address of the patient, name of the doctor, current medication being taken by the patient, etc. In addition, baseline information concerning the patient may also be transmitted to the remote location, via the communication circuitry 74. The doctor or other health professional at the remote location can obtain such data by sending an appropriate signal to the apparatus 10.

The foregoing description and FIG. 1 are intended to provide a general description of the overall structure of the major operational sections of the apparatus 10 of the present invention, along with a brief discussion of some of the specific components employed within those sections. In operating the apparatus 10, the patient or medical professional first determines whether he or she is interested in monitoring cardiac or another type of physiological information (i.e., ECG, EEG, blood pressure, etc.) and then connects the appropriate leads or sensors to the individual being monitored. As previously discussed, when monitoring an ECG, as many as twelve leads could be employed. However, for the purpose of illustrating the operation of the apparatus 10, it will be assumed that only a single lead ECG (including a reference or common lead) has been selected.

The apparatus 10 is preprogrammed to operate as required to receive, store and transmit the selected physiological information. The program is permanently stored in the ROM 56 for recall and utilization by the microprocessor 44 as needed, in the usual manner. However, program variables can be set by the physician. These variables control the parameters at which the device automatically triggers storage of the data. For example, maximum and minimum heart rates for the patient can be stored. If, during use of the device, the rates go beyond the heart rate limits, the monitor automatically stores data and signals the user that storage has occurred. The user could then transmit the captured data.

Top level structure charts showing the progression of the main program and many of the individual sub-programs or 'interrupts' which are utilized in providing a program to control the operation of the apparatus 10 are set forth in the appendix. The structure charts shown exemplify the presently preferred manner of programming the apparatus 10, it being understood that other forms of programs for controlling the apparatus 10 may be developed.

Initially, the microprocessor 44 checks the signal from the ECG lead 12 to insure that the lead is properly attached to the patient. In checking the incoming signal, the microprocessor 44 may monitor the waveform received from the lead 12 to make sure that it is generally periodic in nature and that it is within the range of the patient's ECG, or the microprocessor may perform an ohmic or other such measurement, comparing the result to stored values which indicate proper sensor attachment. If the sensor is properly attached, the microprocessor 44 actuates the programmable amplifier 20 to adjust the amplifier gain to a predetermined level. As previously indicated, in the present embodiment, the gain of the programmable amplifier is increased in a plurality of discrete steps, each step doubling the gain of the previous step. The amplifier gain is increased stepby-step until the amplifier 20 reaches the saturation point. Thereafter, the gain is decreased by one step to provide the desired gain.

The amplified analog signals are then passed through the programmable filter 24 to filter out muscle noise, baseline wander and other noise and are converted to a serial train of digital pulses by the A/D converter. If desired, the blood pressure sensor 32, and other sensors (not shown) connected to the sensor data processor 30 may also be connected to the patient. Signals from these sensors ar also digitized and fed to the microprocessor on a time division multiplexed basis. Since some signals from the other sensors may already be in digital form, these signals may be fed to the multiplexer 28 and from there directly to the microprocessor 44 along line 41.

The digital pulses are received by the microprocessor 44 and are stored a series of predetermined memory locations within the RAM 54. In the present embodiment, the portion of the RAM 54 which is utilized for storing the ECG or other signals holds at least three minutes of signals. The memory is of the circular type so that it constantly stores the immediately preceding period (such as three minutes) of ECG/EEG signals. It will be appreciated by those skilled in the art that the size of the memory of the present embodiment may be either smaller or larger, depending upon a number of factors, including power usage, physical size, etc.

As previously stated, it is often desirable to have the ability to observe a patient's heart activity or other physiological information at particular times, for example, just prior to the occurrence of a symptomatic "event" such as chest pain, or the like. Since the apparatus 10 can constantly monitor and store cardiac and other activity for the preceding period of time, it is possible to retain information concerning pre-event activity. With the presently preferred embodiment, there are two ways that such pre-event information may be retained, one manual and one automatic.

In the case of a patient who realizes the occurrence of an event, a switch (not shown) may be actuated to cause the microprocessor 44 to change the mode of operation from one of continuously recording and storing to one in which only the next period of ECG or other signals are stored. Alternatively, the microprocessor 44 can be programmed to constantly compare incoming ECG signals with a baseline ECG signal. The baseline ECG signal corresponds to an expected "normal" ECG reading for the particular patient, which has been previously stored at a predetermined memory location. The microprocessor conducts a running comparison of the incoming ECG signals with the stored baseline signals. In the event that the comparison indicates a deviation which is greater than a predetermined amount (to be determined by the patient's doctor), the microprocessor itself changes the mode of operation from one of continuously recording and storing, to one in which only the next period of ECG signals are recorded, while the pre-event signals are retained in memory.

Whichever method is used, once the mode of operation has been changed, the incoming ECG signals are received and converted to digital form but no further signals are stored in the memory. Since the memory is capable of storing a large quantity of ECG/EEG signals, the patient's cardiac activity or other activity a period prior to the event and a period after the event can be stored within the memory (each time period can be selected by the physician) for later recall and transmission to the remote location for reconstruction and analysis by a medical professional. For example, if a three minute memory were used, the device could store ECG's one minute prior to the event and two minutes after the event.

A switch (not shown) is also provided to reset the apparatus 10 to the continuously recording mode after the three minutes of information has been transmitted and received at the remote location. The switch may include a lock-out feature which prevents it from being actuated until after a one mv calibration signal and the three minutes of stored ECG information have been transmitted or have been printed out on the printer 63. Alternatively, the microprocessor may be reset to the continuously recording mode by way of a signal received from the remote location (not shown) only after the calibration signal and three minutes of ECG information have been properly received and stored or printed at the remote location. Thereafter, the apparatus 10 operates in the usual manner, continuously storing the previous three minutes of heart activity or other information.

In addition to storing ECG and other signals for later transmission, the apparatus 10 is capable of receiving the signals from the various leads or sensors and immediately transmitting the signals to the remote location to provide "live" or "real time" information. When the device is operating in this manner, the digital signals from the A/D converter 38 are transmitted to the microprocessor 44 but are not stored as previously discussed. Instead, the signals are immediately transmitted from the microprocessor 44 to the communications circuitry 74 for transmission to the remote location. Alternatively, the live or real time signals may also be displayed on the liquid crystal display 68 or may be printed out by the printer 63 for immediate review and analysis by a medical professional who is co-located with the patient. Calibration signals can be transmitted or displayed with the "live" mode through the activation of a switch (not shown).

Alternate Embodiment

The foregoing description relates to the presently preferred embodiment of the invention. However, there may be situations in which it is necessary or desirable to have the capability of storing a greater number of digital signals than may be presently stored in the random access memory (RAM) 54. One way of storing additional physiological information is to expand the storage capability of the existing RAM 54 either by adding additional memory chips or by replacing the existing RAM chip with a chip having greater storage capacity. While there are certain advantages to expanding the storage capability of the memory in this manner, there is the drawback of the expanded memory possibly utilizing additional power, thereby requiring the batteries in the apparatus 10 to be changed with greater frequency. In addition, increasing the size of the memory in this manner may also result in an increased overall size for the apparatus 10 or may make the apparatus more expensive to produce.

A more expedient way of permitting additional physiological information to be stored in the existing RAM 54 is to provide a means for encoding or compressing the physiological information to thereby decrease the amount of memory required for the storing of a given amount of physiological information. One method of encoding such physiological information is described in detail in a paper entitled, "A Computer System for Capturing Transient Electrocardiographic Data," by Kenneth L. Ripley and Jerome R. Cox, Jr., which appeared at pages 439-445 of *Computers in Cardiology*, of the Institute of Electrical and Electronics Engineers Computer Society, in 1976, and which is incorporated herein by reference. The aforementioned paper describes in detail a method of increasing the effective storage capacity of a predetermined size memory by a factor of three, utilizing the technique of encoding digitized data employing a Huffman code. The Huffman code provides for an exact reproduction of all of the original physiological information based on an optimum code set comprised of the smallest number of symbols for a given individual data message. A detailed description of the techniques employed with the Huffman code is available from the aforementioned publication.

Data compression, for example, the Huffman data compression technique, can be conveniently achieved by suitably programming the microprocessor 44 in accordance with the teaching of the aforementioned paper. Incoming physiological signals are processed by the signal conditioning circuitry 14 and are fed to the microprocessor 44. The microprocessor 44 encodes or compresses the data for storage in the RAM 54. When the information is sent to the remote location over the communications system 74, the encoded or compressed data is decoded or decompressed by the base unit (not shown), or by a corresponding portable apparatus for display and consideration by a doctor or other health care professional.

While the present embodiment employs a Huffman encoding technique, it will be appreciated by those skilled in the art that other encoding or data compression techniques could alternatively be employed.

From the foregoing description, it can be seen that the present invention provides a portable, self-contained microprocessor controlled apparatus for monitoring, storing and transmitting detected physiological information. It will be recognized by those skilled in the art that changes may be made to the above-described embodiments of the invention without departing from the broad inventive concepts thereof. It is understood, therefore, that this invention is not limited to the particular embodiment disclosed, but it is intended to cover any modifications which are within the scope and spirit of the invention as defined by the appended claims.

APPARATUS FOR MONITORING, STORING AND TRANSMITTING DETECTED PHYSIOLOGICAL INFORMATION

APPENDIX A

MONITOR

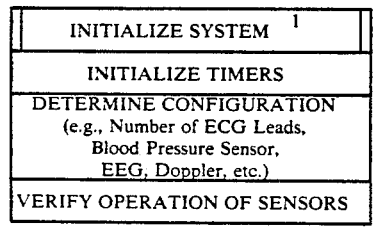

-continued

MONITOR

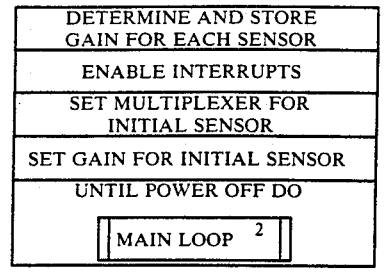

MAIN LOOP

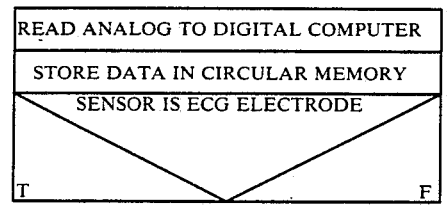

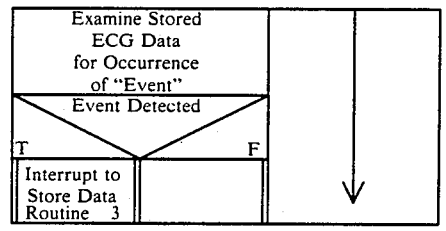

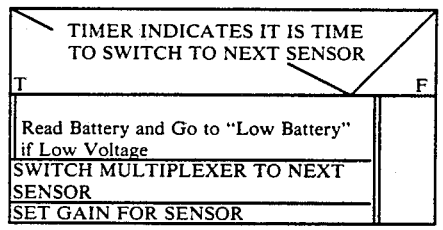

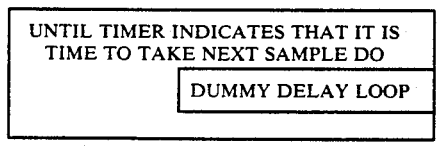

"STORE DATA" INTERRUPT

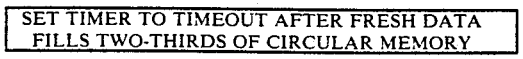

-continued
"STORE DATA" INTERRUPT
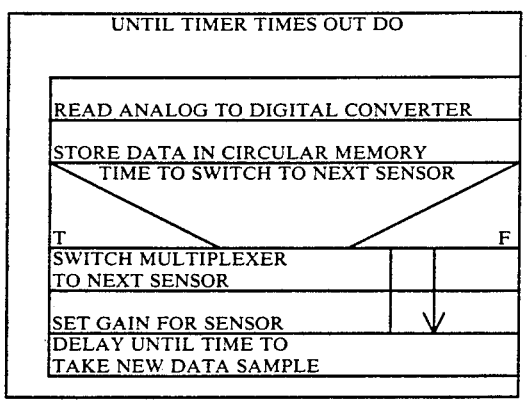
"BLOOD PRESSURE" INTERRUPT
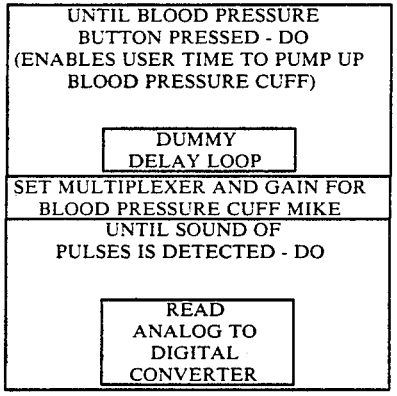
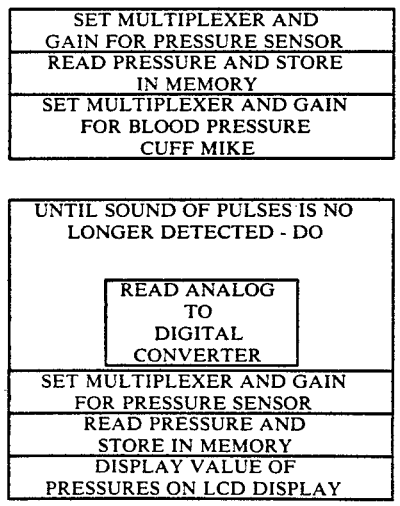
"BLOOD FLOW" INTERRUPT
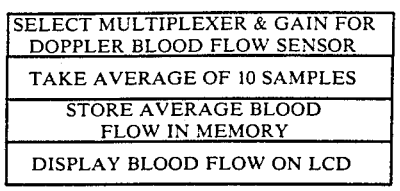
"SEND MEMORY"
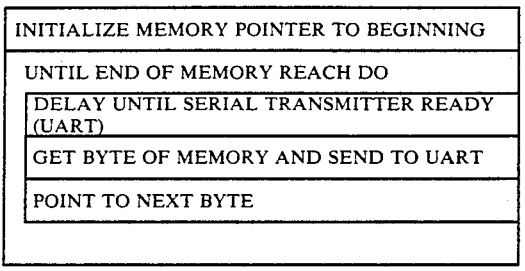
"TRANSMIT DATA" INTERRUPT
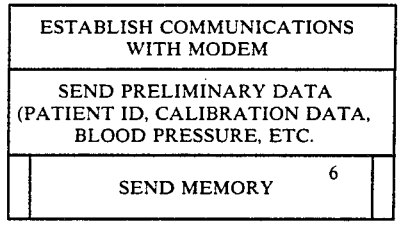
"TRANSMIT LIVE" INTERRUPT
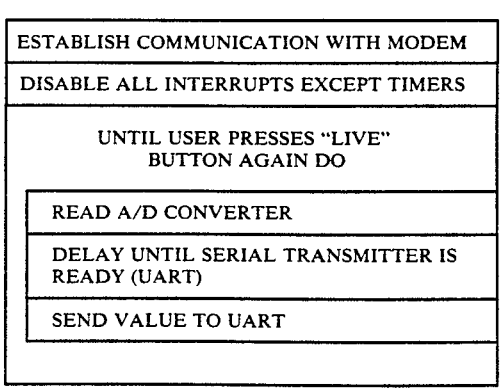

"DISPLAY HEART RATE" INTERRUPT
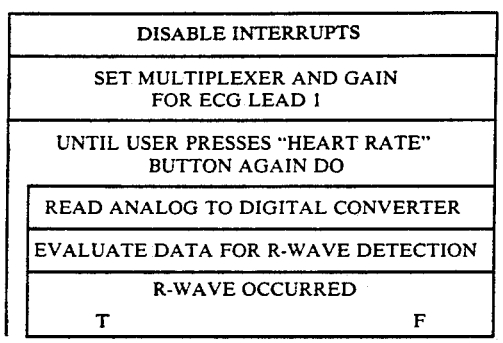
"DISPLAY ECG" INTERRUPT
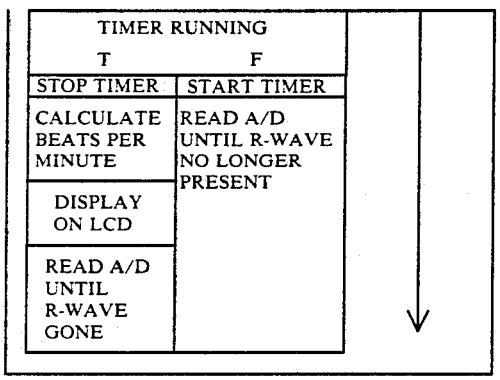
INITIALIZE SYSTEM
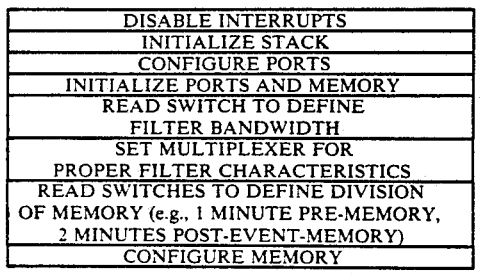
EEG INTERRUPT
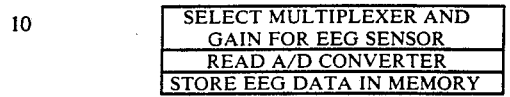
| SELECT MULTIPLEXER AND GAIN FOR EEG SENSOR |
|---|
| READ A/D CONVERTER |
| STORE EEG DATA IN MEMORY |
"LOW BATTERY"
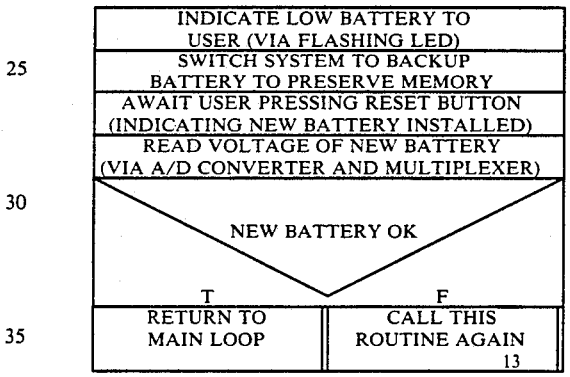
"SELF CHECK" INTERRUPT
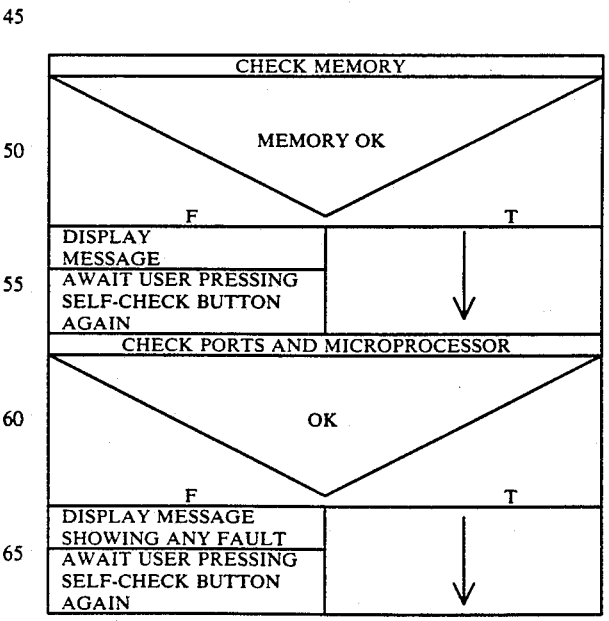

"PRINTER" INTERRUPT

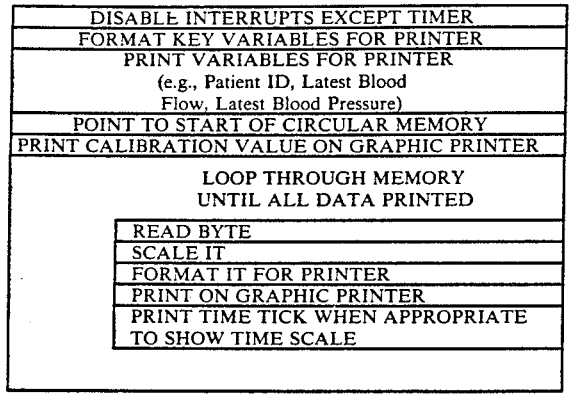

| DISABLE INTERRUPTS EXCEPT TIMER |
| FORMAT KEY VARIABLES FOR PRINTER |
| PRINT VARIABLES FOR PRINTER (e.g., Patient ID, Latest Blood Flow, Latest Blood Pressure) |
| POINT TO START OF CIRCULAR MEMORY |
| PRINT CALIBRATION VALUE ON GRAPHIC PRINTER |
| LOOP THROUGH MEMORY UNTIL ALL DATA PRINTED |
|   READ BYTE |
|   SCALE IT |
|   FORMAT IT FOR PRINTER |
|   PRINT ON GRAPHIC PRINTER |
|   PRINT TIME TICK WHEN APPROPRIATE TO SHOW TIME SCALE |

We claim:

1. A portable, completely self-contained, battery-powered, microprocessor controlled, diagnostic quality apparatus small in size so as to be carried or worn by a patient or other user for monitoring, storing and transmitting detected physiological information of a person being monitored, the apparatus comprising:

means for sequentially receiving analog signals corresponding to heart activity from at least five different cardiac sensors attached at different locations on the body of the person being monitored to provide diagnostic quality cardiac information;

means for receiving analog electrical signals corresponding to blood pressure of the person being monitored from at least one sensor;

means for converting the received analog signals corresponding to heart activity and to blood pressure to a series of digital pulses at a predetermined sampling rate;

memory means for receiving and storing the digital pulses in predetermined memory locations, the memory means being of the circular type and of a predetermined size capable of storing digital pulses equivalent to at least three minutes of diagnostic quality physiological activity so that when the memory means is filled with stored digital pulses, further digital pulses which are received are stored in the memory means by deleting previously stored digital pulses on a first-in, first-out basis, the memory means including means for preventing the deletion of at least a portion of the stored digital pulses corresponding to a period of physiological activity preceding the happening of an event, the memory means continuing to store digital pulses corresponding to physiological activity subsequent to the happening of the event until the memory means is filled, whereupon no further digital pulses are stored;

means for recalling the stored digital pulses from the memory means;

means for receiving the recalled digital pulses from the memory means, for converting the digital pulses to analog signals and for displaying the analog signals to provide a graphic representation of the physiological information;

means for receiving the recalled digital pulses from the memory means and for transmitting the digital pulses to a remote location over a communications system; and means for receiving control signals from the remote location over the communications system and for converting the control signals into digital control pulses, the digital control pulses controlling operation of the apparatus and transferring data to the apparatus.

2. The apparatus as recited in claim 1 wherein the means for receiving the analog electrical signals corresponding to heart activity includes signal conditioning means.

3. The apparatus as recited in claim 2 wherein the signal conditioning means comprises a programmable filter of the band pass type.

4. The apparatus as recited in claim 3 wherein the programmable filter operates in the range of 0.05 Hz to 100 Hz.

5. The apparatus as recited in claim 2 wherein the signal conditioning means comprises a programmable amplifier for automatically adjusting the amplitude of the received analog signal from each sensor to a predetermined amplitude level.

6. The apparatus as recited in claim 5 further including programmed computer means for automatically adjusting the gain of the programmable amplifier upwardly from an initial level by a series of predetermined steps until the programmable amplifier becomes saturated and then adjusting the gain of the programmable amplifier downwardly by one step to establish the predetermined amplitude level for each sensor.

7. The apparatus as recited in claim 6 wherein the computer means adjusts the gain of the amplifier by the predetermines steps, each increasing the gain of the amplifier to be two times the gain of the previous step.

8. The apparatus as recited in claim 7 wherein the gain in each of the predetermined steps of the amplifier is doubled by the computer means decreasing the resistance of a gain resistor by about one-half.

9. The apparatus as recited in claim 6 wherein the predetermined amplitude level for each sensor is stored in a predetermined location within the memory means and is recalled by the computer means to set the gain of the programmable amplifier when signals for the corresponding sensor are received by the means for receiving analog signals.

10. The apparatus as recited in claim 1 wherein the means for receiving the analog signals corresponding to heart activity is adapted for detecting the presence of a pacer signal.

11. The apparatus as recited in claim 10 wherein the pacer detecting means further includes means for generating digital pulses upon the occurrence of a pacer signal, the generated digital pulses being received and stored in the memory means.

12. The apparatus as recited in claim 1 further including printer means for receiving the recalled digital pulses from the memory means and for providing a printed output waveform representative of the physiological information.

13. The apparatus as recited in claim 1 further including means for sequentially receiving analog signals corresponding to brain activity from a plurality of sensors, the brain activity signals being supplied to the means for converting the signals to a series of digital pulses.

14. The apparatus as recited in claim 1 wherein the means for receiving, converting and displaying includes a dot matrix type liquid crystal graphic display device.

15. The apparatus as recited in claim 1 further including means for receiving the digital pulses from the means for converting and for transmitting the received digital pulses to a remote location over a communications system substantially at real time.

16. The apparatus as recited in claim 1 further including encoding means for encoding the digital pulses prior to storage of the digital pulses in the memory means.

17. The apparatus as recited in claim 16 wherein the encoding means utilizes a Huffman code for encoding the digital pulses.

18. A portable, completely self-contained, battery-powered, microprocessor controlled, diagnostic quality apparatus small in size so as to be carried or worn by a patient or other user for monitoring, storing and transmitting detected physiological information of a person being monitored, the apparatus comprising:
means for sequentially receiving analog signals corresponding to brain activity from a plurality of sensors;
means for converting the received analog signals to a series of digital pulses at a predetermined sampling rate;
memory means for receiving and storing the digital pulses in predetermined memory locations, the memory means being of the circular type and of a predetermined size capable of storing digital pulses equivalent to at least three minutes of diagnostic quality physiological activity so that when the memory means is filled with stored digital pulses, further digital pulses which are received are stored in the memory means by deleting previously stored digital pulses on a first-in, first-out basis, the memory means including means for preventing the deletion of at least a portion of the stored digital pulses corresponding to a period of physiological activity preceding the happening of an event, the memory means continuing to store digital pulses corresponding to physiological activity subsequent to the happening of the event until the memory means is filled, whereupon no further digital pulses are stored;
means for recalling the stored digital pulses from the memory means;
means for receiving the recalled digital pulses from the memory means, for converting the digital pulses to analog signals and for displaying the analog signals to provide a graphic representation of the physiological information;
printer means for receiving the recalled digital pulses, for converting the recalled digital pulses into analog form, and for providing a print output waveform representative of the brain wave activity of the patient; and
means for receiving control signals from the remote location over the communications system and for converting the control signals into digital control pulses, the digital control pulses controlling operation of the apparatus and transferring data to the apparatus.

19. A portable, completely self-contained, battery-powered, microprocessor controlled, diagnostic quality apparatus small in size so as to be carried or worn by a patient or other user for monitoring, storing and transmitting detected physiological information of a person being monitored, the apparatus comprising:
means for receiving analog electrical signals corresponding to the patient's physiological activity from at least one sensor secured to the patient;
means for converting the received analog signals to a series of digital pulses at a predetermined sampling rate;
first memory means for initially receiving and storing digital pulses representative of the patient's physiological activity during an initial time period;
second memory means for receiving and storing digital pulses representative of the patient's physiological activity during a current time period;
comparison means for continuously comparing the pulses stored in the first memory means with the pulses stored in the second memory means for determining whether the pulses stored in the second memory means deviate from the pulses stored in the first memory means by more than a predetermined threshold amount;
indicator means for indicating when the deviation exceeds the predetermined threshold amount;
means for recalling the stored digital pulses from the second memory means;
means for receiving the recalled digital pulses from the memory means, for converting the digital pulses to analog signals and for displaying the analog signals to provide a graphic representation of the physiological information;
means for receiving the recalled digital pulses from the second memory means and for transmitting them to a remote location over a communications system; and
means for receiving control signals from the remote location over the communications system and for converting the control signals into digital control pulses, the digital control pulses controlling operation of the apparatus and transferring data to the apparatus.

* * * * *